United States Patent
Kawase et al.

(10) Patent No.: US 9,336,417 B2
(45) Date of Patent: May 10, 2016

(54) OVERTURN DETECTION DEVICE, OVERTURN DETECTION SYSTEM, AND ELECTRONIC DEVICE

(71) Applicants: Tsutomu Kawase, Kanagawa (JP); Michiko Fujii, Tokyo (JP); Moku Naruishi, Kanagawa (JP); Tomoaki Arai, Kanagawa (JP)

(72) Inventors: Tsutomu Kawase, Kanagawa (JP); Michiko Fujii, Tokyo (JP); Moku Naruishi, Kanagawa (JP); Tomoaki Arai, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 429 days.

(21) Appl. No.: 14/022,437

(22) Filed: Sep. 10, 2013

(65) Prior Publication Data
US 2014/0071275 A1 Mar. 13, 2014

(30) Foreign Application Priority Data
Sep. 11, 2012 (JP) ................................. 2012-199354

(51) Int. Cl.
| | |
|---|---|
| G08B 21/00 | (2006.01) |
| G06K 7/00 | (2006.01) |
| B65D 79/02 | (2006.01) |
| G01P 1/12 | (2006.01) |
| G01P 15/03 | (2006.01) |
| B60L 1/00 | (2006.01) |
| A61B 1/00 | (2006.01) |
| G01C 9/10 | (2006.01) |

(52) U.S. Cl.
CPC ...... *G06K 7/00* (2013.01); *B65D 79/02* (2013.01); *G01P 1/127* (2013.01); *G01P 15/036* (2013.01); *A61B 1/00* (2013.01); *B60L 1/00* (2013.01); *G01C 2009/107* (2013.01)

(58) Field of Classification Search
CPC .................................... A61B 1/00; B60L 1/00
See application file for complete search history.

(56) References Cited

U.S. PATENT DOCUMENTS

| | | | |
|---|---|---|---|
| 8,234,993 | B2 | 8/2012 | Naruishi et al. |
| 8,240,270 | B2 | 8/2012 | Naruishi |
| 8,307,775 | B2 | 11/2012 | Naruishi et al. |
| 2011/0090090 | A1* | 4/2011 | Naruishi ................. G01P 1/127 340/666 |
| 2012/0258682 | A1* | 10/2012 | Jang ................... G08B 21/0446 455/404.2 |

FOREIGN PATENT DOCUMENTS

| | | |
|---|---|---|
| EP | 2249166 A2 | 11/2010 |
| EP | 2312324 A2 | 4/2011 |
| JP | 2004-352447 | 12/2004 |
| JP | 4333603 | 8/2006 |

(Continued)

OTHER PUBLICATIONS

European Search Report dated Nov. 26, 2013 in corresponding European patent application No. 13 18 3827.8.

*Primary Examiner* — Shirley Lu
(74) *Attorney, Agent, or Firm* — Cooper & Dunham LLP

(57) ABSTRACT

An overturn detection device includes a housing including four or more display windows, a back-forth direction detector installed on a first position of the housing and displaying a position of a first detection member in a first display part, and a left-right direction detector installed on a second position of the housing and displaying a position of a second detection member in a second display part. Further, the installation positions of the back-forth direction detector and the left-right direction detector in the first and the second positions are not externally and visually recognizable, and at least a part of the first and the second display parts are displayed through the four or more display windows as pattern data.

11 Claims, 19 Drawing Sheets

(56) References Cited

FOREIGN PATENT DOCUMENTS

| | | |
|---|---|---|
| JP | 2011-007771 | 1/2011 |
| JP | 2011-184150 | 9/2011 |
| JP | 2011-237351 | 11/2011 |
| WO | WO2012/035210 | 3/2012 |

* cited by examiner

US 9,336,417 B2

OVERTURN DETECTION DEVICE, OVERTURN DETECTION SYSTEM, AND ELECTRONIC DEVICE

CROSS-REFERENCE TO RELATED APPLICATIONS

The present application is based on claims the benefit of priority under 35 U.S.C §119 of Japanese Patent Application No. 2012-199354 filed on Sep. 11, 2012, the entire contents of which are hereby incorporated herein by reference.

BACKGROUND OF THE INVENTION

1. Field of the Invention

The present invention relates to an overturn detection device and an overturn detection system.

2. Description of the Related Art

In a case where goods such as a precision apparatus (or sensitive equipment) are packed and shipped, if the package body is toppled over during the shipment, the goods in the package body may be damaged due to the overturning. Therefore, an overturn detection device is disposed in the package body to determine whether the package body has toppled over (during the shipment) (see, for example, Japanese Laid-open Patent Publication Nos. 2001-7771 and 2011-237351)

SUMMARY OF THE INVENTION

According to an aspect of the present invention, an overturn detection device includes a housing including four or more display windows, a back-forth direction detector installed on a first position of the housing and displaying a position of a first detection member in a first display part, the first detection member being moved and held in response to turnover of the overturn detection device in the back and forth direction, and a left-right direction detector installed on a second position of the housing and displaying a position of a second detection member in a second display part, the second detection member being moved and held in response to turnover of the overturn detection device in the left and right direction. Further, the installation positions of the back-forth direction detector and the left-right direction detector in the first and second positions are not externally and visually recognizable, and at least parts of the first and second display parts are displayed through the four or more display windows as pattern data.

BRIEF DESCRIPTION OF THE DRAWINGS

Other objects, features, and advantages of the present invention will become more apparent from the following description when read in conjunction with the accompanying drawings, in which.

DETAILED DESCRIPTION OF THE PREFERRED EMBODIMENTS

Figure 1A:
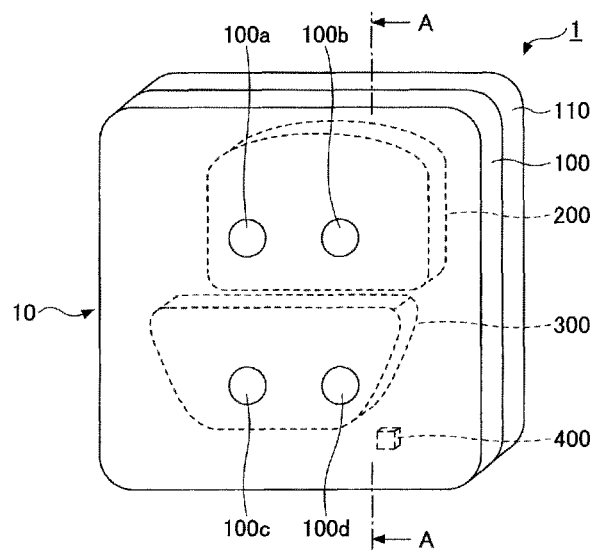
FIG. 1A shows an example overturn detection device according to an embodiment.

In the related-art technologies, whether overturn (overturning) has occurred is visibly recognizable, but the overturn detection device may be intentionally damaged or removed to hide the fact that the overturn occurred.

Further, there is another technique in which a data reading device may be used to read data indicating the position of the detection section and whether overturn has occurred or not. When this technique is used, it is not possible to visibly recognize whether overturn has occurred.

However, by detecting magnetic field lines generated when the data are read by the data reading device, it may become possible to recognize the state of the detecting section and whether the overturn has occurred.

As a result, if it is detected that overturn has occurred, the overturn detection device may also be intentionally damaged or removed to hide the fact that the overturn occurred.

The present invention is made in light of the above problem, and an object of the present invention is to provide an overturn detection device and an overturn detection system capable of detecting the overturn and displaying the overturn using patterns.

In the following, preferred embodiments of the present invention are described with reference to the accompanying drawings. It should be noted that throughout the figures, the same reference numerals may be used to describe the elements having substantially the same functions, and the repeated descriptions thereof may be omitted.

First, an overturn detection device according to an embodiment is described with reference to FIGS. 1A and 1B. Here, FIG. 1A shows an example overturn detection device according to an embodiment and FIG. 1B is a cross-sectional view of the overturn detection device when cut along the line A-A in FIG. 1A.

Figure 1B:
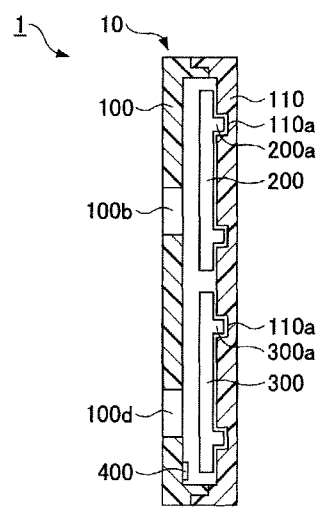
FIG. 1B is a cross-sectional view of the overturn detection device when cut along the line A-A in FIG. 1A.

As shown in FIG. 1A, an overturn detection device 1 includes a housing 10, a back-forth direction detector 200, a left-right direction detector 300, and an ID tag 400. The housing 10 includes a cover part 100 and a bottom part 110. The housing 10 is formed as a hollow member having a substantially rectangular shape when the cover part 100 is engaged with the bottom part 110.

It is desired that the cover part 100 and the bottom part 110 cannot be easily separated from each other so that an overturn detection result cannot be visually recognized. However, the housing 10 may have an opening.

For example, the housing 10 may have an opening on any of the lower, upper, or rear side so that the ID tag 400 can be inserted through the opening to be installed inside the housing 10. Further, for example, the cover part 100 and the bottom part 110 may be made of opaque plastic or the like so that the overturn detection result or the internal structure cannot be externally and visually recognized.

The cover part 100 includes four display windows 100a, 100b, 100c, and 100d. Those display windows 100a, 100b, 100c, and 100d may be through holes passing through the cover part 100, or may further have transparent members sealing the through holes. The shape of the display windows 100a, 100b, 100c, and 100d is not limited to circular, and may be any appropriate shape as long as the display windows may display corresponding display parts formed in the back-forth direction detector 200 and the left-right direction detector 300.

It is desired that the number of the display windows is four or more. In this embodiment, a case is described that the distance between adjacent display windows in the lateral (horizontal) direction is equal to the distance between adjacent display parts formed in the back-forth direction detector 200 and the left-right direction detector 300. However, it should be noted that the present invention is not limited to this configuration. Namely, for example, the display windows may be formed in the housing 10 in accordance with the respective positions of the display parts.

As shown in FIG. 1B, there is a plurality of concave parts 110a formed on the bottom part 110. On the other hand, there are two or more convex parts 200a formed on the back-forth direction detector 200. By engaging the convex parts 200a with the concave parts 110a, the back-forth direction detector 200 is fixed inside the overturn detection device 1.

Similarly, there are two or more convex parts 300a formed on the left-right direction detector 300. By engaging the convex parts 300a with the concave parts 110a, the left-right direction detector 300 is fixed inside the overturn detection device 1.

The back-forth direction detector 200 is installed in a first position of the housing 10, and detects overturning (or, turnover, falling, upset, inclination, impact or the like) in the back and forth (front-back) direction. The installation position of the back-forth direction detector 200 of FIG. 1A is an example of a "first position".

On the other hand, the left-right direction detector 300 is installed in a second position of the housing 10, and detects overturning in the left and right direction. The installation position of the left-right direction detector 300 of FIG. 1A is an example of a "second position".

The ID tag 400 is also installed inside the housing 10. In this embodiment, a case is described where the ID tag 400 is installed on the rear side of the cover part 100. However, the ID tag 400 may be installed in any position. To avoid being damaged, preferably, the ID tag 400 be installed inside the overturn detection device 1.

The ID tag 400 includes (holds) the sensor ID of the overturn detection device 1. The ID tag 400 is an example of a "storage" that holds (stores) identification information of the overturn detection device 1 displaying patterns that will be described below. For example, the "storage" may be Radio Frequency Identification (RFID), Near Field Communication (NFC) or the like. The sensor ID stored in the ID tag 400 may be wirelessly transmitted to a server. By doing this, the server can acquire the sensor ID.

Otherwise, the "storage" may be, for example, a sealing member on which code data such as a bar code and a QR code (registered trademark) are displayed. In this case, the sensor ID which is coded as the bar code or QR code is stored. The coded sensor ID may be read as image data and transmitted to the server. By doing this, the server can acquire the sensor ID.

Further, to avoid an input error, preferably, the sensor ID may be detected (double-checked) based on both bar code and REID. Namely, at least, the "storage" may be either the ID tag or the sealing member having the code data.

Back-Forth Direction Detector

Next, the back-forth direction detector 200 according to an embodiment is described with reference to FIGS. 2 through 6.

Figure 2:
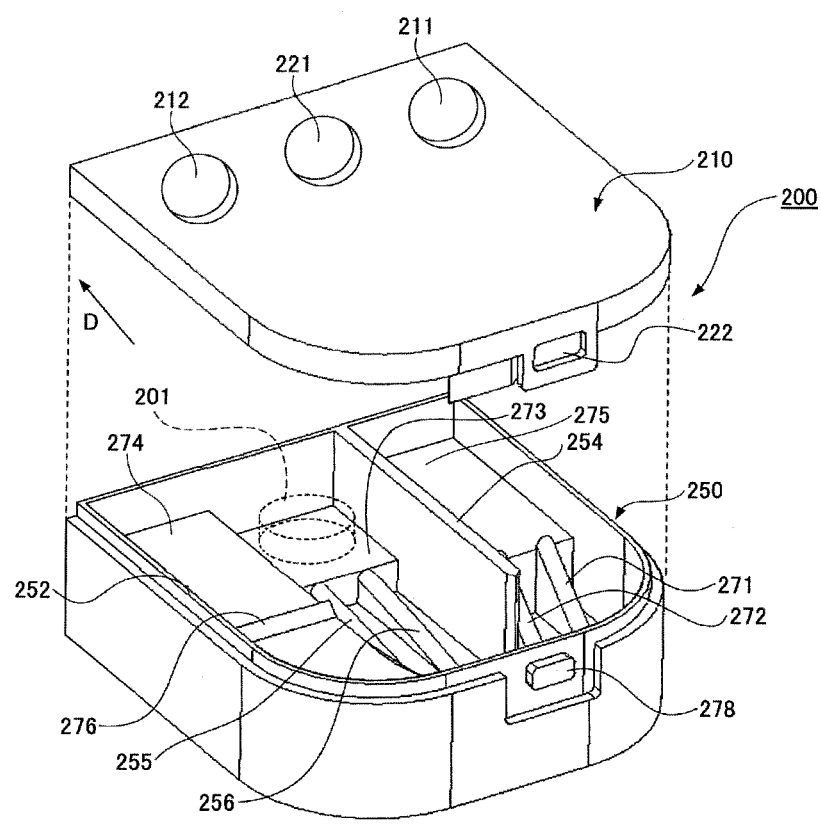
FIG. 2 is an example exploded perspective view of a back-forth direction detector according to an embodiment.
Figure 3:
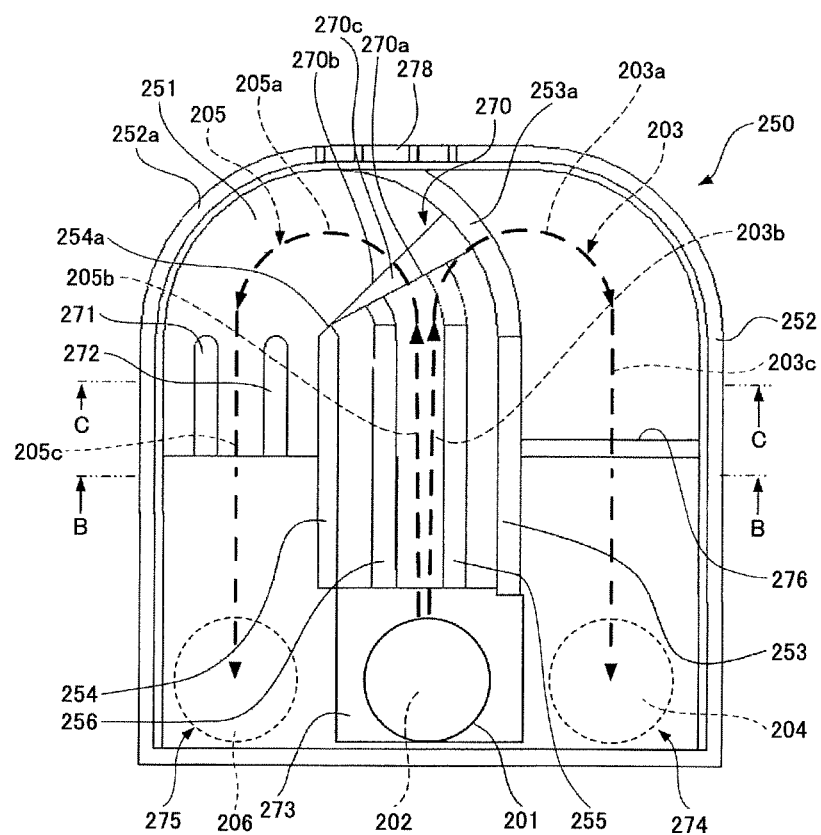
FIG. 3 shows an example lower case of the back-forth direction detector according to an embodiment.
Figure 4:
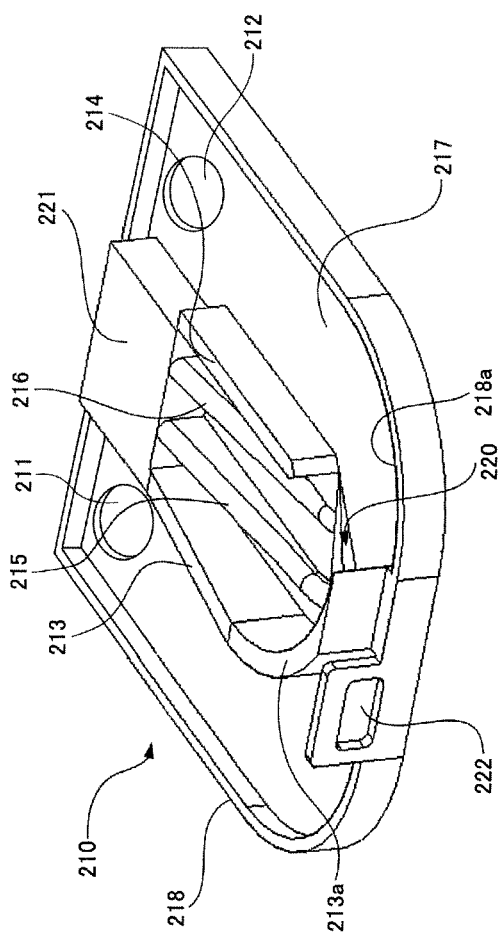
FIG. 4 shows an example upper case of the back-forth direction detector according to an embodiment.

FIG. 2 is an example exploded perspective view of the back-forth direction detector 200 according to this embodiment. FIG. 3 is a top view showing an example lower case of the back-forth direction detector 200 according to this embodiment. FIG. 4 is a top view showing an example upper case of the back-forth direction detector 200 according to this embodiment.

Figure 5:
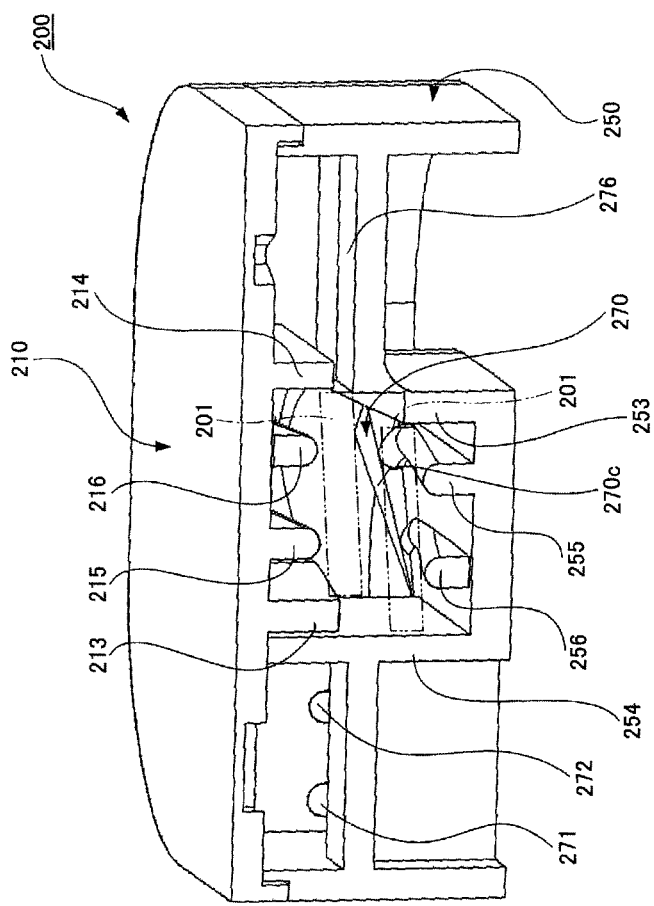
FIG. 5 is an example cross-sectional perspective view of the back-forth direction detector when cut along the line B-B of FIG. 3.
Figure 6:
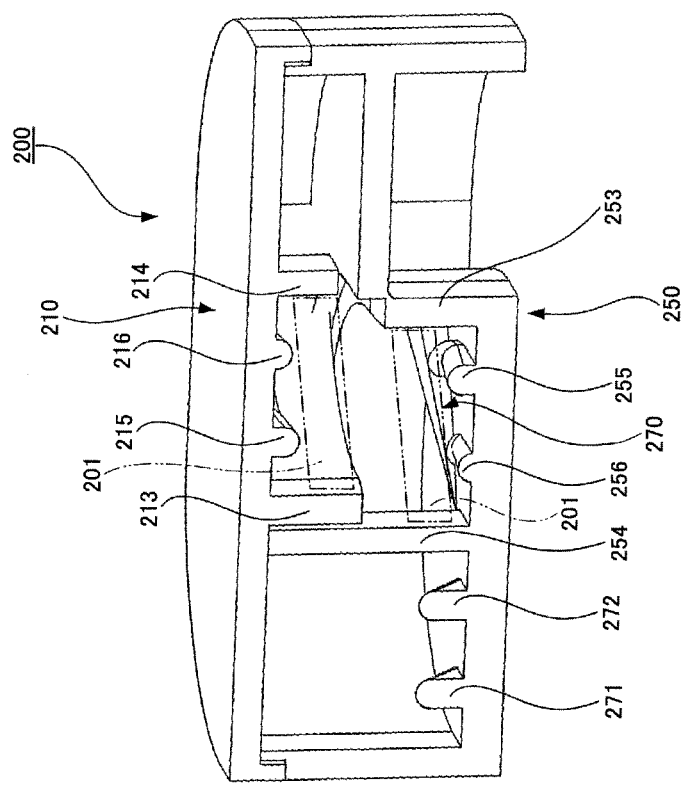
FIG. 6 is an example cross-sectional perspective view of the back-forth direction detector when cut along the line C-C of FIG. 3.

FIG. 5 is an example cross-sectional perspective view of the back-forth direction detector 200 when cut along the line B-B of FIG. 3. FIG. 6 is an example cross-sectional perspective view of the back-forth direction detector 200 when cut along the line C-C of FIG. 3.

As shown in FIG. 2, the back-forth direction detector 200 includes a first case that is formed by engaging an upper case 210 with a lower case 250. Inside the first case, there is disposed a weight (weight member) 201 that corresponds to a "first detecting member". The weight 201 may be a tablet-type member made of aluminum and may have color.

Further, in the back-forth direction detector 200, there are formed an upper-case-side moving path 203 (corresponding to a "first moving path", see FIG. 3) and a lower-case-side moving path 205 (corresponding to a "second moving path") formed between the upper case 210 and the lower case 250, so that the weight 201 travels through the paths 203 and 205.

When the back-forth direction detector 200 in a standing state where the arrow "D" from the detector 200 in FIG. 2 is directed downward is tilted (turned over) on the upper case 210 side, the weight 201 travels from its initial position 202 to an upper-case side impact detecting position 204 corresponding to its display position through the upper-case-side moving path 203 in FIG. 3.

Then, the back-forth direction detector 200 is returned to the standing state, the weight 201 can be seen through the display part 212 of the upper case 210 facing the weight disposing part 274 of FIG. 3.

Further, the upper-case-side moving path 203 includes a folding (U-shape) path 203a through which the weight 201 travels in an arc shape in the moving direction towards the upper-case side impact detecting position 204, a straight path 203b guiding the weight 201 from the initial position 202 to the folding path 203a, and a straight path 203c guiding the weight 201 from the folding path 203a to the upper-case side impact detecting position 204.

Similarly, when the back-forth direction detector 200 in the standing state is directed downward is tilted on the lower case 250 side, the weight 201 travels from the initial position 202 to a lower-case side impact detecting position 206 through the lower-case-side moving path 205. Then, the back-forth direction detector 200 is returned to the standing state, the weight 201 can be seen through the display part 211 of the upper case 210 facing the weight disposing part 275.

As described above, when the weight 201 can be seen in the display part 212 of the upper case 210, this means that the back-forth direction detector 200 was tilted (turned over) on the upper case 210 side. Similarly, when the weight 201 can be seen in the display part 211 of the upper case 210, this means that the back-forth direction detector 200 was tilted (turned over) on the lower case 250 side.

On the other hand, when the weight 201 can be seen in the display part 221 of the upper case 210, this means that the back-forth direction detector 200 was not tilted (turned over) in the back and forth (front-back) direction. Here, the display parts 221, 211, and 212 corresponds to a "first display part" indicating whether a "first weight" was moved through "first or second moving path".

Further, the lower-case-side moving path 205 includes a folding (U-shape) path 205a through which the weight 201 travels in an arc shape in the moving direction towards the lower-case side impact detecting position 206, a straight path 205b guiding the weight 201 from the initial position 202 to the folding path 205a, and a straight path 205c guiding the weight 201 from the folding path 205a to the lower-case side impact detecting position 206.

Further, in this example, the straight path 203b of the upper-case-side moving path 203 is superimposed on the straight path 205b of the lower-case-side moving path 205 in top view.

Further, as shown in FIG. 4, the upper case 210 includes a plate-like bottom plate 217 and an outer wall 218 on the outer side of the bottom plate 217. Further, the display parts 211 and 212 are formed on the bottom plate 217. Further, on the rear side of the upper case 210, standing wall parts 213 and 214 are formed in a standing manner as the corresponding parts of the upper-case-side moving path 203 to serve as "moving path defining parts". Further, in the inner side of the standing wall parts 213 and 214, several rails 215 and 216 are formed in a standing manner to guide the weight 201.

The upper-case-side moving path 203 is surrounded (defined) by the standing wall parts 213 and 214 and the curved outer wall 218 of the upper case 210 and is formed in the lower case 250. Here, the folding path 203a is formed between a curvedly-formed edge part 213a of the standing wall part 213 and an arc part 218a of the outer wall 218, and the straight path 203b is formed between the standing wall parts 213 and 214.

Further, a concave part 221 depressed toward the lower case 250 is formed in the bottom plate 217 of the upper case 210. The concave part 221 is disposed at the position facing a convex part 273 (FIG. 3) of the lower case 250 facing (corresponding to) the initial position 202 of the weight 201 in the lower case 250, in a manner that distance between the upper case 210 and the lower case 250 at the initial position 202 is such that the weight 201 disposed at the initial position 202 can be stably disposed between the upper case 210 and the lower case 250.

There is a latch hole 222 (FIG. 2) formed on the upper case 210 so as to be latched with the lower case 250. Further, there is a fan-like weight defining guide part 220 formed on the top (tip) parts of the rails 215 and 216. The weight defining guide part 220 is formed to smoothly guide the weight 201 from the straight path 203b to the folding path 203a and prevents the reverse movement of the weight 51 having traveled into the folding path 203a.

Next, the lower case 250 is described. The lower case 250 is made of, for example, a colored synthetic resin member. An outer wall 252 is formed in a standing manner on the outer side of a bottom plate 251. Further, standing wall parts 253 and 254 are formed in a standing manner on the bottom plate 251. The standing wall parts 253 and 254 serve as "moving path defining parts" defining the lower-case-side moving path 205. In the inside standing wall parts 253 and 254, several rails 255 and 256 are formed in a standing manner to guide the weight 201.

The lower-case-side moving path 205 is surrounded (defined) by the standing wall parts 253 and 254 and the curved arc part 252a of the standing wall part 253 of the lower case 250. Here, the folding path 205a is formed between a curvedly-formed edge part 253a of the standing wall part 253 and an arc part 252a of the outer wall 252, and the straight path 205b is formed between the standing wall parts 253 and 254. Further, a convex part 273 protruding toward the upper case 210 is formed in the bottom plate 251. A latch protruding part 278 (FIG. 2) is formed on the lower case 250 to be latched with the latch hole 222.

With reference to FIGS. 5 and 6 showing cross-sectional views when cut along the lines B-B and C-C, respectively, the embodiment is further described.

As schematically shown in FIGS. 5 and 6, the height of the rail 215 disposed on the outer perimeter side of the folding path 203a (FIG. 3) is set to be greater than the height of the rail 216 disposed on the inner perimeter side of the folding path 203a. Further, it is designed so that when the weight 201 is in contact with the standing wall part 214 on the inner perimeter side of the folding path 203a, the top of the rails 215 and 216 can be in contact with the weight 201.

Similarly, the height of the rail 255 disposed on the outer perimeter side of the folding path 205a (FIG. 3) is set to be greater than the height of the rail 256 disposed on the inner perimeter side of the folding path 205a. Further, it is designed so that when the weight 201 is in contact with the standing wall part 254 on the inner perimeter side of the folding path 205a, the top of the rails 255 and 256 can be in contact with the weight 201.

By doing this, when the weight 201 travels through the upper-case-side moving path 203 and the lower-case-side moving path 205, the weight 201 is tilted. As a result, the weight 201 may travel more smoothly and the thickness of the back-forth direction detector 200 may be reduced.

Further, there is a fan-like weight defining guide part 270 formed on the top (tip) parts of the rails 255 and 256. The weight defining guide part 270 includes an edge end 270a (FIG. 3) on the rails 255 and 256 side, another edge end 270b (FIG. 3) on the side opposite to the rails 255 and 256 side, and a tilted part 270c formed between the edge ends 270a and 270b. The edge end 270a is formed to have the same height as those of the top (tip) parts of the rails 255 and 256.

On the other hand, the edge end 270b is formed in a manner that the height difference between the edge end 270b and the bottom plate 251 is decreased as the position is closer to the inner side. The tilted part 270c formed between the edge ends 270a and 270b is formed in a manner that the height of the tilted part 270c is decreased when the position is closer to the inner side and there is no height difference between the tilted part 270c and the bottom plate 251 at the position where the tilted part 270c is in contact with the top (tip) part 254a of the standing wall part 254.

By doing this, the weight defining guide part 270 may smoothly guide the weight 201 from the straight path 205b to the folding path 205a and prevent the reverse movement of the weight 51 from the folding path 205a back to the straight path 205b.

In the weight disposing part 274, there is disposed a weight movement preventing protrusion 276 extending in the direction crossing with the moving direction of the weight 201 to prevent the reverse movement of the weight 51 back to the straight path 203c.

Further, the weight movement preventing protrusion 276 includes a tilted part formed on the straight path 203c side so that the weight 201 can easily move into the upper-case side impact detecting position 204, and a vertical surface on the weight disposing part 274 side so that the weight 201 once entered into the upper-case side impact detecting position 204 is not returned to the straight path 203c.

On the other hand, there are tilted rails 271 and 272 formed in the straight path 205c of the lower-case-side moving path 205 on the weight disposing part 275 side, so as to guide the weight 201 traveling through the straight path 205c of the lower-case-side moving path 205 to be placed on the weight disposing part 275.

Further, the end parts on the weight disposing part 275 side of the tilted rails 271 and 272 are formed so as to have slightly greater height than that of the weight disposing part 275, so that the weight 201 once disposed in the weight disposing part 275 is not returned to the straight path 205c.

By having the structures described above, when the back-forth direction detector 200 is tilted (turned over) on the upper case 210 side (i.e., in the forth direction), the weight 201 is guided from the initial position 202 while being in contact with the rails 215 and 216 of the upper case 210 along the straight path 203b of the upper-case-side moving path 203. In this case, the weight 201 is inclined (tilted), moves (travels) on the rails 215 and 216, and stops beyond the weight defining guide part 220.

Next, when the back-forth direction detector 200 is returned to the original position (state), the weight 201 is guided by the end edge of the weight defining guide part 220 and moved in the folding path 203a, so that the weight 201 is accommodated in the weight disposing part 274 of the lower case 250 and disposed in the upper-case side impact detecting position 204. As a result, the traveled weight 201 can be seen through the display part 212.

On the other hand, when the back-forth direction detector 200 is tilted (turned over) on the lower case 250 side (i.e., in the back direction), the weight 201 is guided from the initial position 202 while being in contact with the rails 255 and 256 of the lower case 250 along the straight path 205b of the lower-case-side moving path 205. In this case, the weight 201 is inclined (tilted), moves (travels) on the rails 255 and 256, and stops beyond the weight defining guide part 270.

Next, when the back-forth direction detector 200 is returned to the original position (state), the weight 201 is guided by the end edge of the weight defining guide part 270 and moved in the folding path 205a to be guided by the tilted rails 271 and 272, so that the weight 201 is accommodated in the weight disposing part 275 of the lower case 250 and disposed in the lower-case side impact detecting position 206. As a result, the traveled weight 201 can be seen through the display part 211.

According to this embodiment, in any of the cases where the back-forth direction detector 200 is tilted (turned over) in the back and forth directions, the weight 201 is moved from the position of the display part 221 to upward first and further moved to any of the display parts 211 or 212. Therefore, it may become possible to reliably detect the turnover (tilt) of the back-forth direction detector 200 in the back and forth direction.

Figure 7:
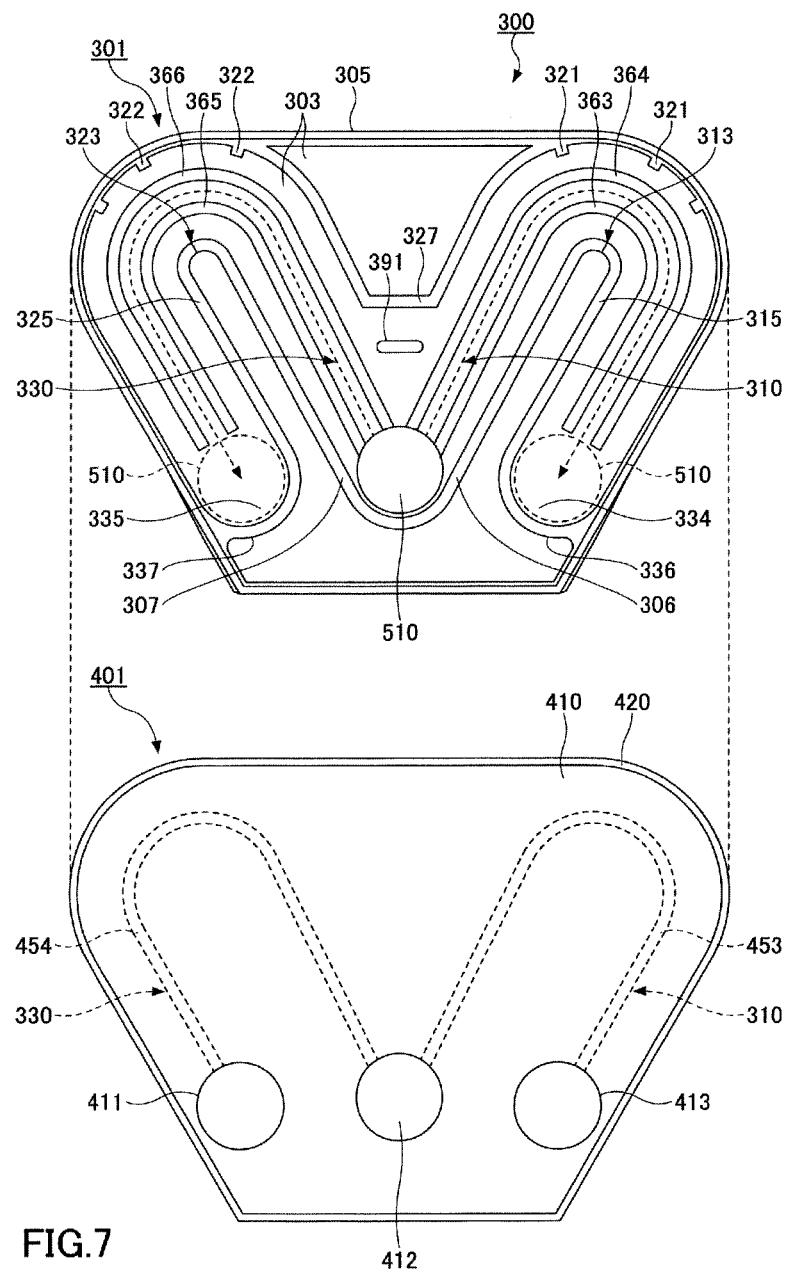
FIG. 7 is an example exploded view of a left-right direction detector according an embodiment.

Next, the left-right direction detector 300 is described with reference to FIG. 7. FIG. 7 is an example exploded view of the left-right direction detector according an embodiment. As shown in FIG. 7, the left-right direction detector 300 includes a second case having a rear case 301 and a front case 401 sealing the front side surface of the rear case 301.

In the second case, there is a weight 510 (corresponding to a "second detecting member") that changes its position due to the overturning (or, turnover, falling, upset, inclination, impact or the like) in the left and right direction of the left-right direction detector 300.

The rear case 301 is made of a synthetic resin member and includes a bottom plate 303 and a standing rim part 305 formed in a standing manner on the periphery of the bottom plate 303. In the rear case 301, curved right-side moving path 310 and left-side moving path 330, through which the weight 510 travels, are formed on the respective sides of the weight 510.

On the end parts of the right-side moving path 310 and left-side moving path 330, a right-side weight holding part 334 and a left-side weight holding part 335 are formed by rib members 336 and 337, respectively.

In the initial position, the weight 510 is held by a right-side plate member 306 and a left-side plate member 307. The right-side plate member 306 is integrally formed with a right-side plate member 315 via a folding part 313 as a single member. Similarly, the left-side plate member 307 is integrally formed with a left-side plate member 325 via a folding part 323 as a single member.

Especially, each of the right-side plate member 315 and the left-side plate member 325 may be formed by bending a single elastic thin plate made of stainless steel. By doing this, the inner circumference side of the right-side moving path 310 and left-side moving path 330 is defined.

On the bottom plate 303, right-side weight guiding rails 363 and 364 and left-side weight guiding rails 365 and 366 are formed along the right-side moving path 310 and the left-side moving path 330, respectively. Those guiding rails are integrally formed with the bottom plate 303. Further, to reduce the contact resistance with the weight 510, the guiding rails are formed in a manner that the shape of the contacting side of the guiding rails is arc-shaped.

Further, on the right-side weight guiding rails 363 and 364 and left-side weight guiding rails 365 and 366, respective reverse movement preventing protrusions (not shown) to prevent the reverse movement of the weight 510 are formed.

Further, on the bottom plate 303, a stop plate 391 is formed to prevent the weight 510 from being bounced. In the standing rim part 305, in the areas close to the right-side moving path 310 and the left-side moving path 330, a plurality of protrusions 321 and a plurality of protrusions 322, respectively, are formed to prevent the movement of the weight 510 caused by the bouncing of the weight 510.

Above the stop plate 391, a plate-like member 327 is formed so that the plate-like member 327 along with standing rim part 305 defines the outer circumference side of the right-side moving path 310 and left-side moving path 330.

Next, the front case 401 is described. The front case 401 is made of a synthetic resin member and includes a plate member 410, which seals (covers) the entire front-side surface of the rear case 301, and a protruding part 420 formed on the outer periphery of the plate member 410 to determine the position of the front case 401 relative to the rear case 301.

On the front case 401, display parts 411, 412, and 413 to display the position of the weight 510 are formed. Those display parts 411, 412, and 413 correspond to a "second display part" indicating whether the left-right direction detector 300 was tilted in the left and right directions of the left-right direction detector 300 and which direction the left-right direction detector 300 was tilted based on the movement of the weight 510 passing through the right-side moving path 310 or the left-side moving path 330.

Specifically, the weight 510 travels through the right-side moving path 310 or the left-side moving path 330 and held in the right-side weight holding part 334 or the left-side weight holding part 335 when the left-right direction detector 300 is tilted in the right or left direction, respectively. Therefore, when the weight 510 is displayed through the display part 412, the left-right direction detector 300 was not tilted. However, when the weight 510 is displayed through the display parts 411 or 413, the left-right direction detector 300 was tilted (turnover occurs) in the left or right direction, respectively.

On the rear case 301 side of the plate member 410, a single right-side weight guiding rail 453 and a single left-side weight guiding rail 454 corresponding to the right-side moving path 310 and the left-side moving path 330 are formed. The right-side weight guiding rail 453 and the left-side weight guiding rail 454 are integrally formed with the plate member 410.

Further, to reduce the contact resistance with the weight 510, those weight guiding rails 453 and 454 are formed in a manner that the shape of the cross-section on the surface side facing the weight 510 is arc-shape. Further, on each of the weight guiding rails 453 and 454, reverse movement preventing protrusions (not shown) to prevent the reverse movement of the weight 510 are formed. The reverse movement preventing protrusions are disposed (formed) at the positions relative to the positions of the reverse movement preventing protrusions formed on the rear case 301.

In the initial state where no falling or turnover occurs, as shown in FIG. 7, the weight 510 is held under the stop plate 391 formed to prevent the weight 510 from being bounced. When the left-right direction detector 300 is tilted (turnover occurs) in the right direction, the weight 510 is moved through the right-side moving path 310 while being guided by the right-side plate member 306 and dropped down to and is held in the right-side weight holding part 334.

On the other hand, when the left-right direction detector 300 is tilted (turnover occurs) in the left direction, the weight 510 is moved through the left-side moving path 330 while being guided by the left-side plate member 307 and dropped down to and is held in the left-side weight holding part 335.

By having the structure described above, in any of the cases where the left-right direction detector 300 is tilted (turnover occurs) in the left and right directions, the weight 510 is moved upward relative to the left-right direction detector 300 first. Then, when the left-right direction detector 300 is tilted (turnover occurs) in the left or right direction, the weight 510 is moved from the position of the display part 412 to the display part 413 or 411, respectively. Therefore, it becomes possible to reliably detect the turnover in the left and right directions.

Patterning of Display

As described above, the housing 10 covers the entire back-forth direction detector 200 and left-right direction detector 300 so that the first and second positions cannot be seen. Further, in this embodiment, there are four display windows formed on the housing 10.

Those four display windows are used to display patterns which are formed by using the display parts 221, 211, and 212 of the back-forth direction detector 200 and the display parts 411, 412, and 413 of the left-right direction detector 300. The patterning will be described in detail with reference to FIG. 8.

Figure 8:
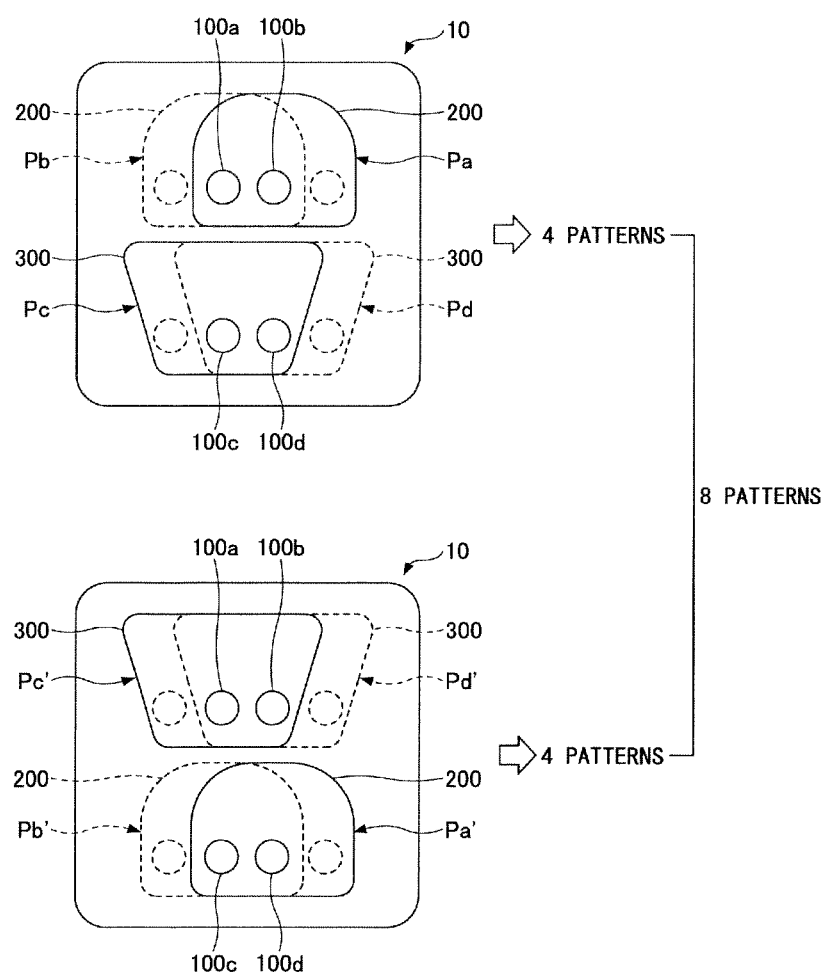
FIG. 8 is a view exemplarily illustrating the number of display windows of a housing and the number of patterns according to an embodiment.

FIG. 8 exemplarily illustrates the number of display windows of a housing and the number of patterns according to this embodiment. In the upper part of FIG. 8, the back-forth direction detector 200 is fixed relative to the housing 10 in a manner that the positions of the display windows 100a and 100b of the housing 10 correspond to the positions of the two display parts from the right end (i.e., the display parts 212 and 221) or the left end (i.e., the display parts 221 and 211) of the back-forth direction detector 200.

Each of the positions "Pa" and "Pb" shown in the upper part of FIG. 8 is an example of the "first position" where the back-forth direction detector 200 is fixed to the housing 10.

In the upper part of FIG. 8, the left-right direction detector 300 is fixed relative to the housing 10 in a manner that the positions of the display windows 100c and 100d of the housing 10 correspond to the positions of the two display parts from the right end (i.e., the display parts 412 and 413) or the left end (i.e., the display parts 412 and 411) of the left-right direction detector 300.

Each of the positions "Pc" and "Pd" shown in the upper part of FIG. 8 is an example of the "second position" where the left-right direction detector 300 is fixed to the housing 10.

Therefore, as shown in the upper part of FIG. 8, when the back-forth direction detector 200 is disposed in the upper part of the housing 10 and the left-right direction detector 300 is disposed in the lower part of the housing 10, four patterns (combinations) indicating which of overturn displays can be seen through the display windows 100a, 100b, 100c, and 100d can be displayed based on the four combinations of the first and second positions (Pa, Pc), (Pa, Pd), (Pb, Pc), and (Pb, Pd).

In the same manner, in lower part of FIG. 8, the left-right direction detector 300 is fixed relative to the housing 10 in a manner that the positions of the display windows 100a and 100b of the housing 10 correspond to the positions of the two display parts from the right end or the left end of the left-right direction detector 300.

Each of the positions "Pc'" and "Pd'" shown in the lower part of FIG. 8 is an example of the "second position" where the left-right direction detector 300 is fixed to the housing 10.

Further, the back-forth direction detector 200 is fixed relative to the housing 10 in a manner that the positions of the display windows 100c and 100d of the housing 10 correspond to the positions of the two display parts from the right end or the left end of the back-forth direction detector 200.

Each of the positions "Pa'" and "Pb'" shown in the lower part of FIG. 8 is an example of the "first position" where the back-forth direction detector 200 is fixed to the housing 10.

Therefore, as shown in the lower part of FIG. 8, when the left-right direction detector 300 is disposed in the upper part of the housing 10 and the back-forth direction detector 200 is disposed in the lower part of the housing 10, four patterns (combinations) indicating which overturn displays can be seen through the display windows 100a, 100b, 100c, and 100d can be displayed based on the four combinations of the first and second positions (Pa, Pc), (Pa, Pd), (Pb, Pc), and (Pb, Pd).

Based on the above descriptions, when the number of display windows of the housing is four, the state of the display parts of the back-forth direction detector 200 and the left-right direction detector 300 can be displayed by using any of eight patterns display methods (FIG. 8).

In FIG. 8, for explanatory purposes, the back-forth direction detector 200 and the left-right direction detector 300 are drawn using a solid or dotted line. Actually, however, the back-forth direction detector 200 and the left-right direction detector 300 are covered by the housing 10. Namely, it is not possible to externally and visually detect the installation positions of the back-forth direction detector 200 and the left-right direction detector 300 in the housing 10.

Figure 9:
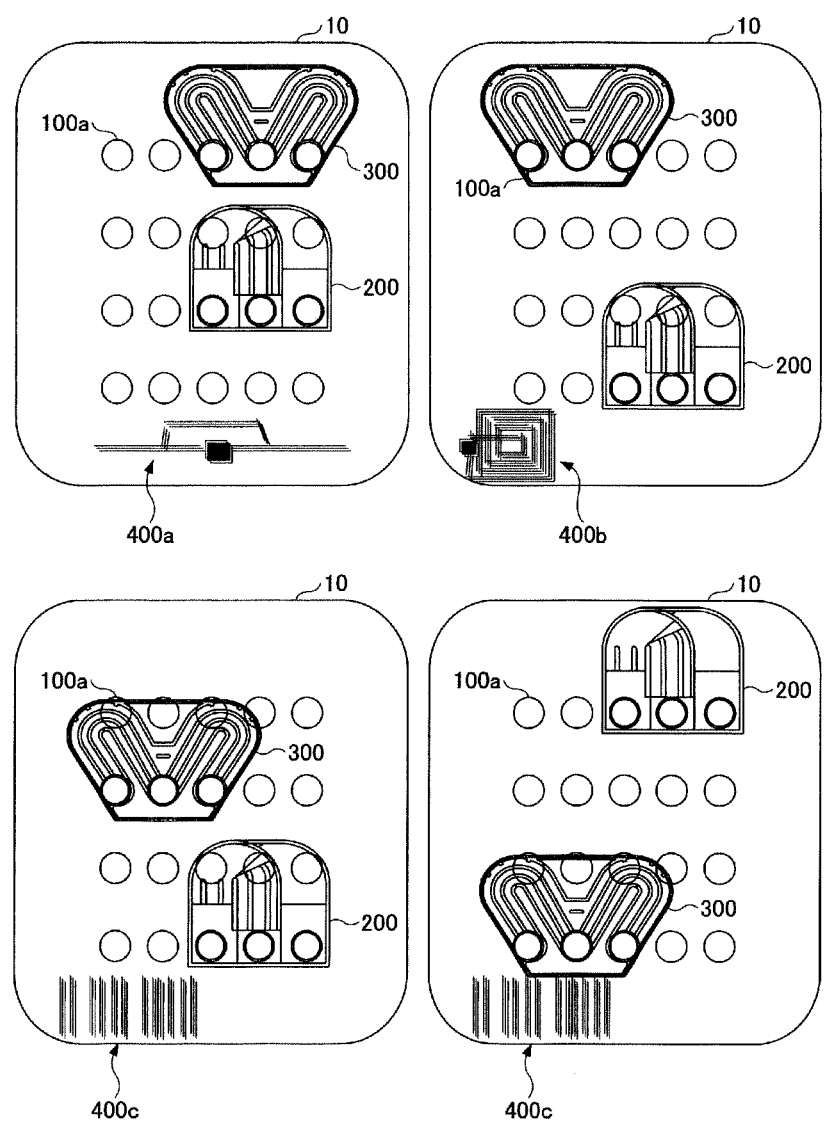
FIG. 9 is another view exemplarily illustrating the number of display windows of the housing and the number of patterns according to an embodiment.

When the number of display windows formed on the housing 10 is increased, the number of display patterns is accordingly increased. FIG. 9 is another view exemplarily illustrating the number of display windows of the housing and the number of patterns according to an embodiment. For example, as shown in FIG. 9, when 20 display windows are formed on the housing 10, it becomes possible to display the states of the back-forth direction detector 200 and the left-right direction detector 300 using one of as many as 108 patterns of display methods.

In the overturn detection device 1 according to this embodiment, the "first position" where the back-forth direction detector 200 is fixed and the "second position" where the left-right direction detector 300 is fixed are changeable. Therefore, the display pattern using four or more display windows can be changed by changing at least one of the first and second positions.

Therefore, in the overturn detection device 1 according to this embodiment, the turnover can be detected and the information indicating whether the turnover occurs may be displayed (visually recognized) using a pattern. It should be noted it is difficult to recognize the (meaning of the displayed) pattern in this embodiment for a person who does not know how the back-forth direction detector 200 and the left-right direction detector 300 are fixed to the housing 10 in advance.

Therefore, it may become possible to reduce the risk of damaging or removing the overturn detection device 1 after turnover occurs.

As examples of the "storage", FIG. 9 shows cases of an REID tag 400a in the UHF band, an RFID tag (NEC) 400b in the HF band, and a bar code 400c. For example, in a film-sheet type RFID tag, the IC chip, that is a circuit including a receiving and transmitting circuit, ID number generation circuit and the like, is sandwiched by two laminate films. Such a film-sheet type RFID tag may wirelessly communicate with a terminal device in an overturn detection system described below.

Overturn Detection System

In an overturn (tilt, impact) detection system according to an embodiment, the overturn detection device 1 wirelessly communicates with a cellular phone, so the cellular phone reads the sensor ID identifying the overturn detection device 1 and stored in the ID tag. The sensor ID read by the cellular phone is transmitted to a server along with a pattern image of the display windows imaged (captured) by the cellular phone.

When a label indicating the code data such as a bar code is used (attached), the code data such as the bar code, which are imaged by the cellular phone, are transmitted to the server along with the image of the display windows imaged by the cellular phone.

The server acquires (extracts) the sensor ID of the overturn detection device 1 from the image of the bar code. Then, the server compares the pattern data acquired based on the image analysis of the display window with the initial pattern data previously registered in association with the overturn detection device 1 to be identified based on the sensor ID.

Based on the comparison result, the server determines whether the overturn detection device 1 is turned over (tilted, inclined, impacted, or the like) and also the direction(s) of the turnover.

An overturn detection system 2 according to this embodiment determines whether a product was turned over by attaching the overturn detection device 1 to the product. In the description, the cellular phone is described as an example of a terminal device. However, any appropriate device having an image reading (capturing) function and a communication function may alternatively be used.

Figure 10:
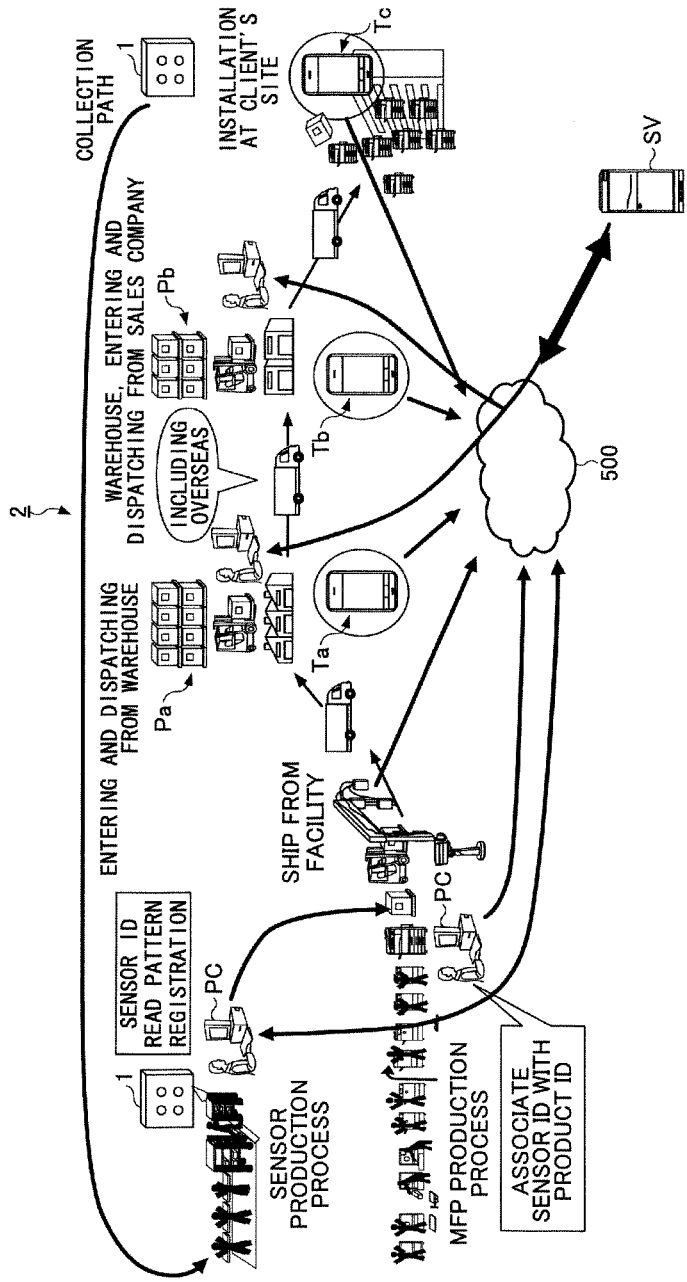
FIG. 10 is a drawing illustrating an example entire overturn detection system according to an embodiment.

FIG. 10 illustrates an example entire overturn detection system according to this embodiment. As shown in FIG. 10, in the sensor production process, a manager registers data indicating the sensor ID identifying the overturn detection device 1 and initial pattern data of the display windows into the REID. The sensor ID corresponds to identification data for identifying the overturn detection device.

The initial pattern data refer to an initial value of the pattern data displayed based on the display windows of the overturn detection device 1 identified by the identification data at the initial condition of the shipment. Here, the pattern data of the display windows are formed based on the initial positions of the weights 201 and 510. The sensor ID is registered in the ID tag, and the pattern data of the display windows at the shipment are transmitted to a server SV via the cellular phone and stored in association with the sensor ID in the server SV.

Here, a Multi Functional Peripheral (MFP) is described as an example of a product. However, it should be noted that the overturn detection device 1 may be attached to (installed in) any appropriate product. In the MFP production process, a product ID identifying the MFP is registered. The product ID is transmitted to the server SV via the cellular phone and registered in association with the sensor ID in the server SV.

The overturn detection device 1 manufactured (completed) in the sensor production process is attached to the shipping box in which the MEP is packed. To that end, an adhesive seal (not shown) is attached to the rear surface of the housing 10 of the overturn detection device 1. By using the adhesive seal, the overturn detection device 1 is attached to the shipping box including the MFP and shipped.

By doing this, at the shipment from the factory, the manager associates the sensor ID with the initial pattern data, and transmits the sensor ID in association with the initial pattern data to the server by using a personal computer (PC) installed in a site for the MFP production process or sensor production process via a network 500. However, when the ID tag, the sensor ID, the product ID, and the initial pattern data are stored in association with each other, it is not always necessary to transmit those data to the server SV.

After the shipment and before the delivery to the client, the product may be placed in and dispatched from one or more warehouses. For example, in the case of FIG. 10, when the product (MFP) is placed in and dispatched from the warehouse at point "Pa", the manager of "Pa" captures images including the display windows of the overturn detection device 1 using a camera function of a cellular phone Ta when the product (MFP) is placed in and when the product (MEP) is dispatched from the warehouse. Then, the manager transmits the images to the server SV.

Similarly, when the product (MFP) is paired in and dispatched from the sales company at point "Pb", the manager of "Pb" captures images including the display windows of the overturn detection device 1 using a camera function of a cellular phone Tb when the product (MFP) is placed in and when the product (MFP) is dispatched from the sales company. Then, the manager transmits the images to the server SV.

After that, the product (MFP) is installed at the designated site of the client. When the product (MFP) is installed, the manager of the installation site captures an image including the display windows of the overturn detection device 1 using a camera function of a cellular phone Tc and transmits the captured image to the server SV via the network 500.

The server SV receives images of the overturn detection device 1 transmitted from the cellular phones Ta, Tb, and Tc, performs image processing on the received images to acquire respective pattern data, and compares the respective pattern data with the initial pattern data registered in advance to determine whether the turnover occurred and the direction of the turnover if the turnover occurred.

By doing this, in the overturn detection system 2 according to this embodiment, the overturn detection device 1 is formed in a manner that it is not possible to externally and visually determine whether the turnover occurred and it is the server side on which it is possible to determine whether the turnover occurred.

Therefore, it may become possible to remove the risk that the overturn detection device 1 is damaged or removed in the shipping process of the overturn detection device 1 due to the occurrence of the turnover of the overturn detection device 1.

Further, after the product (MFP) is shipped via the points "Pa" and "Pb" and installed, the overturn detection device 1 attached to the shipping box may be collected for reuse in the sensor production process.

Server's Functional Configuration

Figure 11:
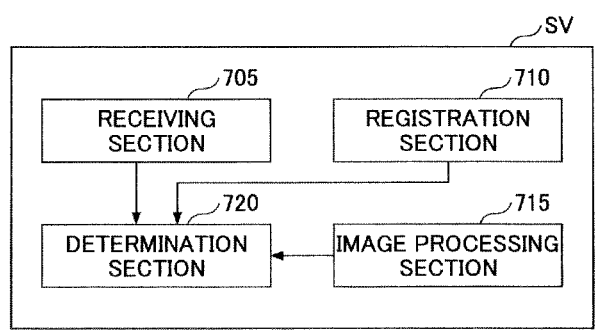
FIG. 11 is an example functional block diagram of a server according to an embodiment.

Next, the functions of the server SV that determine whether the turnover occurred are described with reference to FIG. 11. FIG. 11 is an example functional block diagram of the server SV according to this embodiment. As shown in FIG. 11, the server SV includes a receiving section 705, a registration section 710, an image processing section 715, and a determination section 720.

The cellular phone reads (captures) the image including all the display windows and the sensor ID of the overturn detection device 1 and transmits the captured image and the sensor ID to the server SV.

To that end, the cellular phone reads (acquires) the sensor ID from at least one of the ID tag and the code data attached to the overturn detection device 1, and transmits the acquired sensor ID along with the captured image of the display windows to the server SV.

In the transmission, it is preferable that the captured image of the display windows be encrypted before the transmission to the server SV. Similarly, it is preferable that the sensor ID be encrypted and stored in the RFID or the like, so that even a third party who reads the sensor ID cannot easily decrypt the sensor ID.

The receiving section 705 receives the image and the sensor ID transmitted from the cellular phone. The registration section 710 registers in advance the identification data of the overturn detection device 1 attached to a product (MFP) in association with the pattern data of the overturn detection device 1 attached to the product (MFP). The image processing section 715 performs image processing on the received images.

The determination section 720 compares the initial pattern data stored in association with the sensor ID corresponding to the received sensor ID among the sensor IDs registered in the registration section 710 with the pattern data recognized based on the received images, and based on the comparison results, determines whether the overturn detection device 1 (i.e., the product (MFP)) was turned over and the direction of the turnover.

Figure 12:
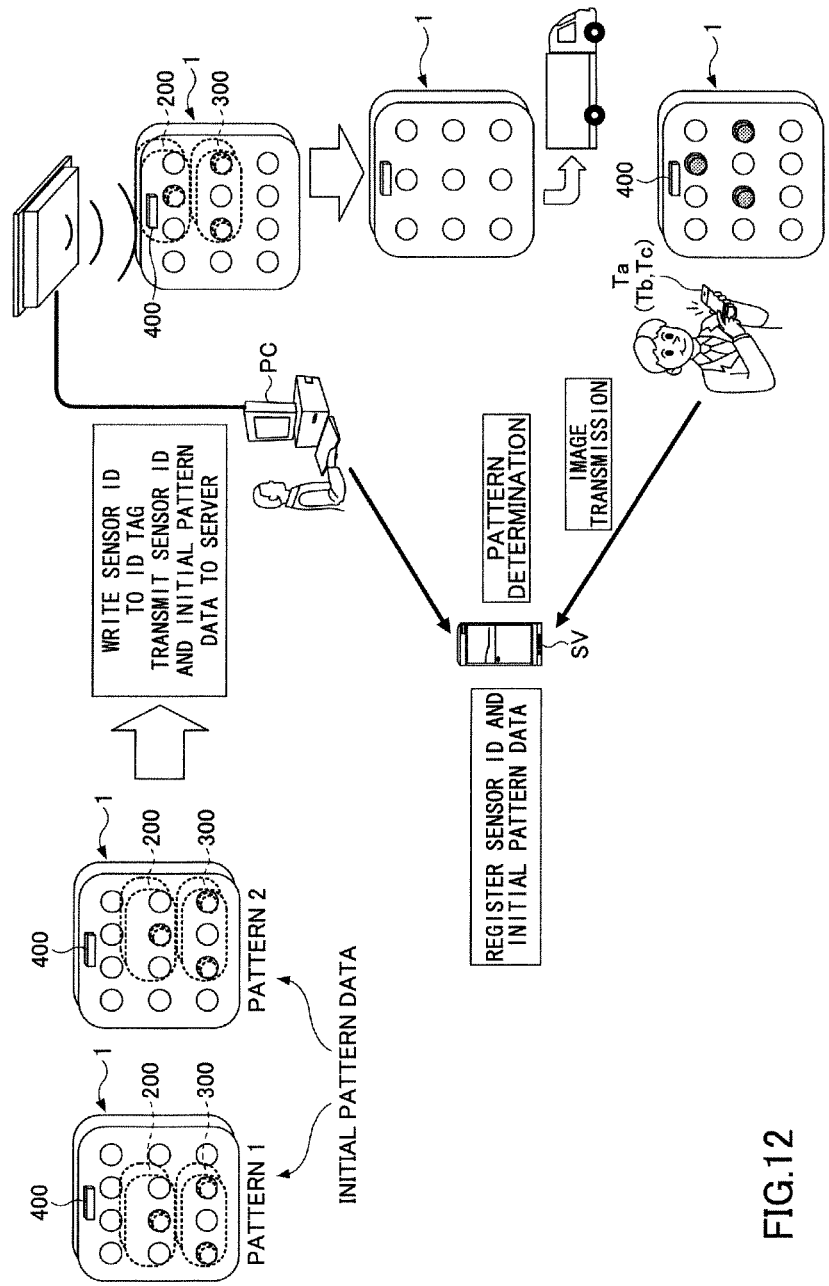
FIG. 12 illustrates example pattern determination according to an embodiment.

One specific example of pattern determination by the determination section 720 is described with reference to FIG. 12. FIG. 12 illustrates example pattern determination according to this embodiment.

As shown in FIG. 12, when the positions of the back-forth direction detector 200 and the left-right direction detector 300 relative to the housing 10 (i.e., the first and second positions) are determined, the initial pattern is automatically determined. In this case, for example, if the positions of the back-forth direction detector 200 and the left-right direction detector 300 differ, corresponding different initial patterns are generated.

The manager of the sensor production process registers the sensor ID in the ID tag. Further, the manager transmits the sensor ID and the initial pattern data to the server SV using a (manager's) PC. The server SV stores the received initial pattern data in association with the sensor ID. In this case, the product ID to which the overturn detection device 1, identified by the sensor ID, is attached may be stored in association with the sensor ID.

After the shipment of the product with the overturn detection device 1 attached thereto, the images of the display windows of the overturn detection device 1 captured by the cellular phones Ta, Tb, and Tc at the sites "Pa", "Pb", and finally installed site are transmitted to the server SV.

The determination section 720 compares the initial pattern data stored in association with the sensor ID acquired from the bar code in the received image or the received sensor ID with the pattern data recognized by performing the image processing on the received image, and determines that no turnover occurred when the compared images are identical as the results of the comparison, but determines that turnover occurred if any of the data as a result of the comparison are not identical (equivalent).

Further, the determination section 720 may further determine in which of the back and forth and left and right directions the overturn detection device 1 (i.e., product) has been turned over. Namely, based on the registered initial pattern data in the registration section 710, the determination section 720 identifies the first position indicating the position of the back-forth direction detector 200 and the second position indicating the position of the left-right direction detector 300.

The determination section 720 determines whether any of the weights 201 and 510 have been moved and the moved direction that turnover occurred based on the first and second positions and the pattern data that are different from the corresponding initial pattern data to determine in which of the back and forth and left and right directions the turnover occurred.

Further, based on the product ID registered in the registration section 710, the determination section 720 determines the product corresponding to the overturn detection device 1 that is determined to have been turned over.

Figure 13:
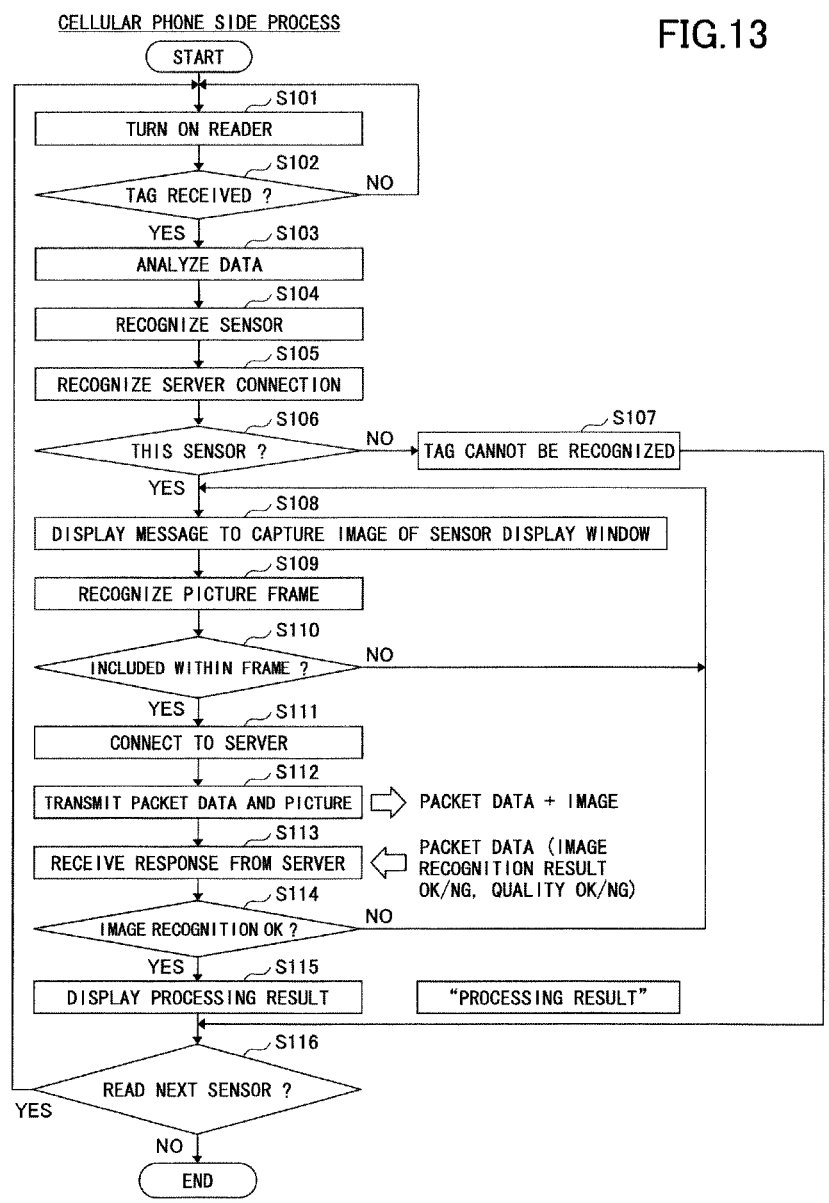
FIG. 13 is a flowchart illustrating an overturn detection process according to an embodiment.
Figure 14:
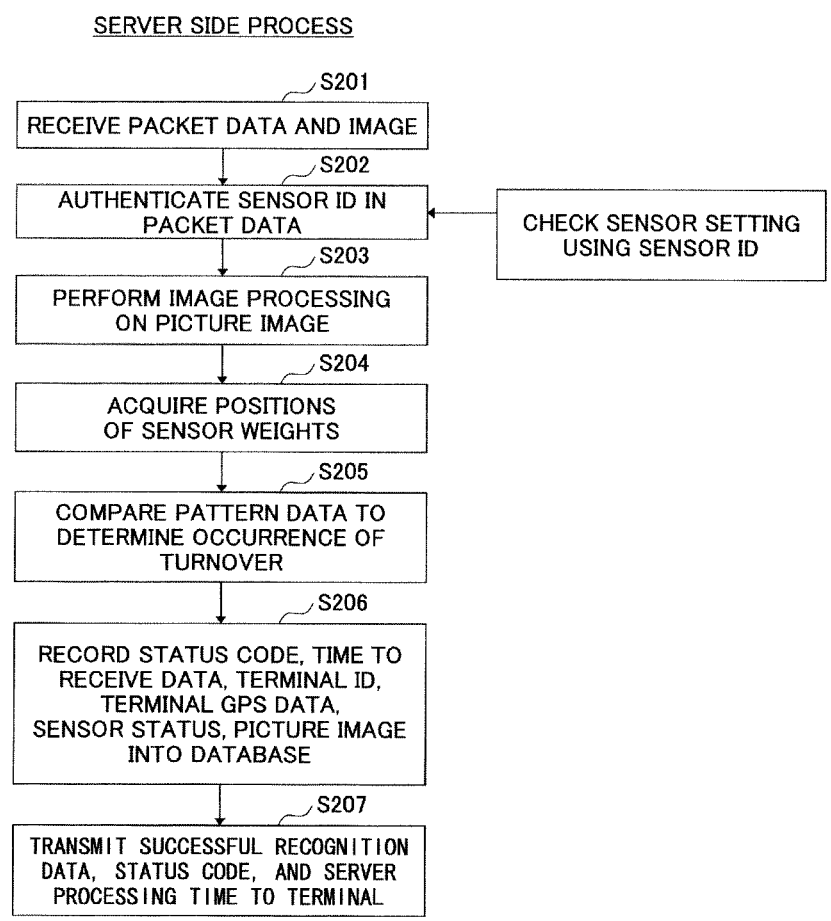
FIG. 14 is another flowchart illustrating the overturn detection process according to the embodiment.

Next, an overturn detection process according to this embodiment is described with reference to FIGS. 13 and 14. FIG. 13 is an example flowchart of the overturn detection process (on the cellular phone side) according to this embodiment. The process of FIG. 13 may be performed by any of the cellular phones Ta, Tb, and Tc. However, it is preferable that the process be performed by the cellular phone Ta or Tb. FIG. 14 is an example flowchart of the overturn detection process (on the server side) according to this embodiment.

In the process on the cellular phone side in FIG. 13, the cellular phone is started up and the reading function of the cellular phone is activated (step S101). The cellular phone establishes near field communications and determines whether it is possible to receive data from the ID tag (step S102). Until the data can be received, the process of steps S101 and S102 are repeated. After receiving the data, the cellular phone analyzes the received data (step S103), recognizes the sensor ID (step S104), and recognizes the connection server SV (step S105).

When determining that the recognized sensor ID is not a target sensor of this system (No in step S106), the cellular phone display a message "Not recognizable ID tag" on its display screen (step S107), and determines whether to read the next sensor (step S116). When determining not to read a sensor any more, the process ends. When determining to read the next sensor, the process goes back to step S101.

In step S106, when determining that the recognized sensor ID is a target sensor of this system (Yes in step S106), the process goes to step S108 and the cellular phone displays a message "Please take a picture of sensor display windows" on the display screen. Then, the manager takes a picture (image) of the display windows of the overturn detection device 1 using the cellular phone. The cellular phone recognizes a picture frame (step S109), so that the cellular phone determines whether the entire display windows are placed within the picture frame (step S110).

When it is determined that the entire display windows are not placed within the picture frame (No in step S110), the process goes back to step S108 to repeat the steps S108 through S110.

When determining that the entire display windows are placed within the picture frame (Yes in step S110), the cellular phone establishes connection with the server SV (step S111), and transmits the packet data, which includes the sensor ID, and the captured picture (image) to the server SV (step S112).

Referring to the process on the server side of FIG. 14, the server SV receives the packet data and the image (picture) (step S201). Next, the server SV compares the sensor ID registered in the registration section 710 with the sensor ID in the packet data, and searches for the sensor ID corresponding to the sensor ID in the packet data (step S202).

The server SV performs image processing on the received image (picture) (step S203), acquires (recognizes) the positions of the weight 201 in the back-forth direction detector 200 and the weight 510 of the left-right direction detector 300, so as to acquire the pattern data formed of the weights 201 and 510 (step S204).

Based on the searched-for result in step S202, the server SV compares the initial pattern data registered in association with the sensor ID corresponding to the sensor ID read as image data in the packet data with the pattern data identified (recognized) based on the received image (step S205). When determining that those patterns are the same as each other, the server SV determines that no turnover occurred, but when determining that those patterns are different from each other, the server SV determines that turnover occurred (step S205). In the latter case, based on the data of the difference, the server may further determine in which direction the turnover occurred.

The server SV records a state code indicting whether a turnover occurred and in which direction the turnover occurred, time when the image is received, the terminal ID (cellular phone ID) of the transmission source of the image, terminal GPS information, a sensor status, and the picture image into a desired database DB (step S206). The server SV transmits the data indicating that the pattern has been successfully recognized, the state code, the processing time by the server SV and the like to the cellular phone (step S207).

Referring back to the process on the cellular phone side in FIG. 13, the cellular phone receives the packet data from the server SV (step S113). The packet data include the data indicating whether the image is successfully recognized or not (OK or NG) and the data indicating whether the image quality is good enough or not (OK or NG).

As a result of the determining whether the image is successfully recognized or not (OK or NG), when the result is NG (No in step S114), the process goes back to step S108, and the process from step S108 through step S114 is repeated. When determining that the image is successfully recognized (OK) (Yes in step S114), the process goes to step S115. In step S115, the cellular phone displays the processing result on its screen.

For example, a processing result "No turnover detected", "Turnover detected in the right direction", "Turnover detected in the front direction" or the like is displayed. When no further sensor is to be read, the process ends (step S116).

Modified example of overturn detection process

Figure 15:
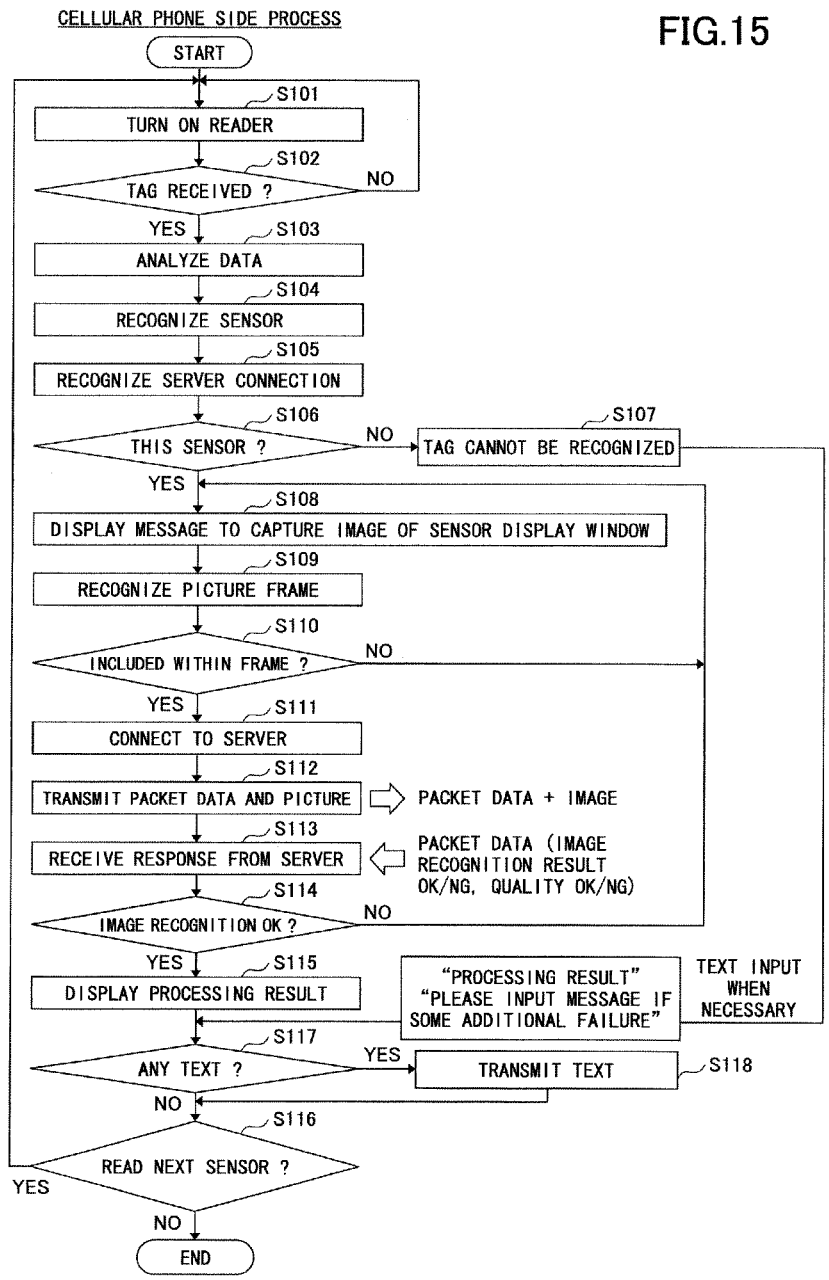
FIG. 15 is a flowchart illustrating an overturn detection process according to a modified embodiment.
Figure 16:
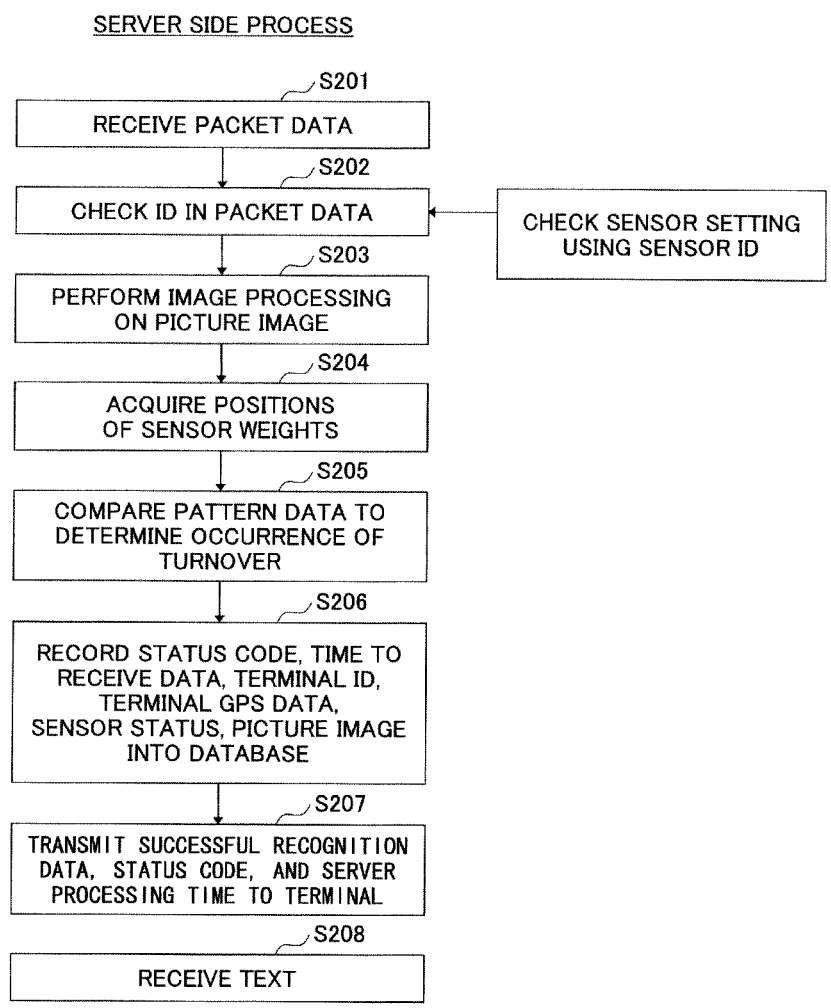
FIG. 16 is another flowchart illustrating the overturn detection process according to the modified embodiment.

Next, an overturn detection process according to modified example of this embodiment is described with reference to FIGS. 15 and 16. FIG. 15 is a flowchart illustrating an overturn detection process (on the cellular phone side) according to an modified example in this embodiment. The process in FIG. 15 may be performed by any of the cellular phones Ta, Tb, and Tc. However, it is preferable that the process be performed by the cellular phone Tc. FIG. 16 illustrates the overturn detection process performed by the server SV.

In this modified example, the process differs from the process described as the overturn detection process of this embodiment in that when the processing result is displayed in step S115, text may be input via the cellular phone when necessary. Therefore, this difference is mainly described and the repeated descriptions may be omitted.

When the process on the cellular phone side in FIG. 15 is started, the cellular phone performs steps S101 to S114 and the server SV performs steps S201 to S207.

In step S115, the cellular phone displays the processing result and prompts the data transmission from the cellular phone to the server SV. In this case, for example, along with the message indicating the processing result such as "No turnover detected", "Turnover detected in the right direction", "Turnover detected in the front direction" or the like, a message for calling attention such as "Please input message when you find external damage, etc." so as to prompt the input of text (message) to be reported to the server SV.

In response to the message, when any text (message) is input (step S117), the text (message) is reported from the cellular phone to the server SV (step S118).

On the other hand, in the process on the server SV side in FIG. 16, the receiving section 705 receives the reported text (message) (step S208). For example, a message such as "Shipping box is crushed", "Product is damaged", "Product appears to not be damaged although we heard from server that turnover already occurred" may be reported from the cellular phone Tc.

In this regard, the server SV may receive the text (message) reporting, for example, a turnover state. When the report is received from the cellular phone Tc at the final installation side of the product, such report may be valuable because the report directly explains the final state of the product.

As described above, in the overturn detection system 2 according to this embodiment and the modified example of this embodiment, the turnover is detected by using the overturn detection device 1 by which it is not possible to externally and visually determine whether the turnover occurred. Therefore, it may become possible to reduce the risk of damaging or removing the overturn detection device 1 after turnover has occurred.

Further, if the overturn detection device 1 is used as a stand-alone device, recording and tracing of the turnover are manually performed. However, when the overturn detection system 2 according to this embodiment or the modified example of this embodiment is used, the recognition of the pattern data displayed in the overturn detection device 1 and the determination whether turnover occurred are automatically processed. Therefore, an error or mistake in recording and omission of recording may be effectively avoided and the operational cost be reduced.

Especially, in the overturn detection system 2 according to this embodiment and the modified example of this embodiment, the states of the product at the sites where the pictures (images) are captured by the cellular phones are reported. Therefore, based on the data at each site, the server SV may determine where the turnover occurred. As a result, it may become possible to use those data to determine whether to exchange the product and who is responsible for the damage and turnover.

Further, when the ID tag is attached to the overturn detection device 1, it becomes possible to store the sensor ID and product ID in the ID tag. Further, the registered sensor ID and product ID may be accumulated in the ID tag. On the other hand, when a bar code is attached to the overturn detection device 1, it becomes possible to store only the sensor ID as the code data. Therefore, when the bar code or the QR code is used, it is desired to manage the product ID on the server SV side.

Example of System Application

In the overturn detection system 2 according to this embodiment and the modified example of this embodiment, the data may be stored in the sensor (ID tag), cellular phones Ta, Tb, and Tc, and server SV as described below.

Figure 17:
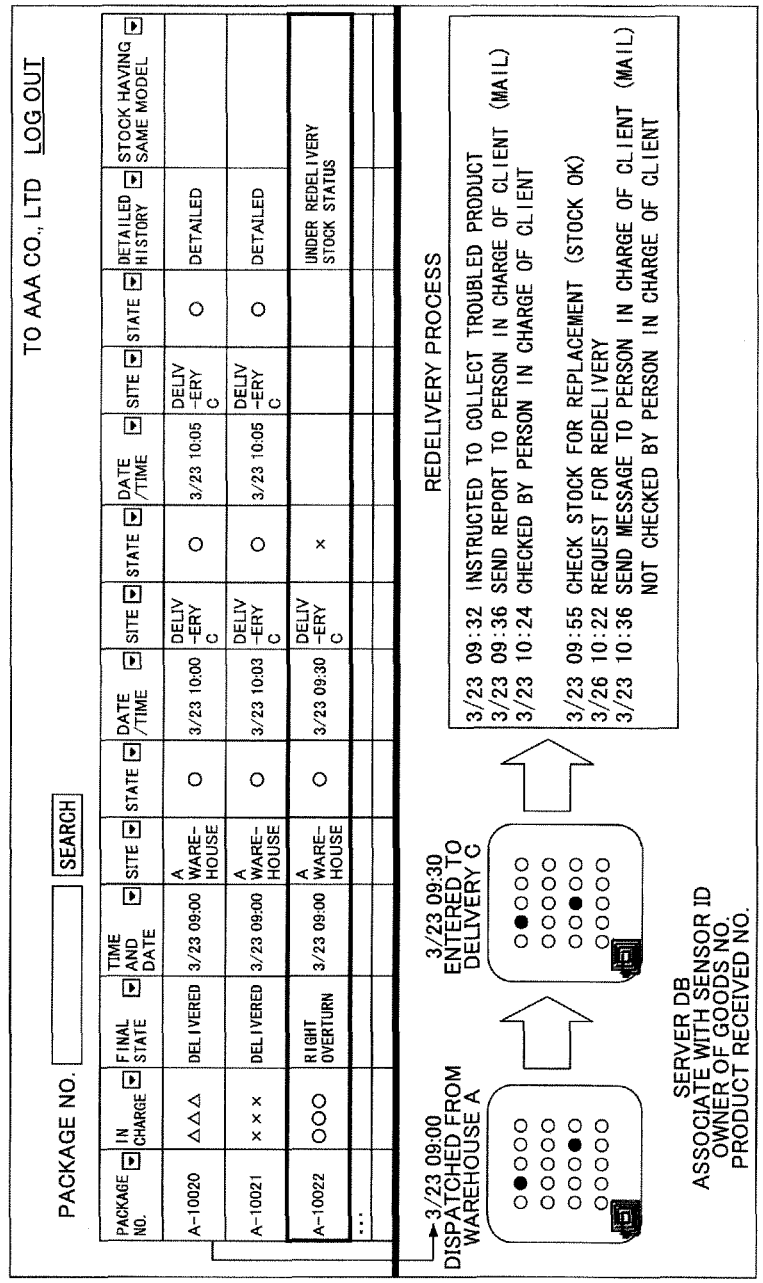
FIG. 17 is an example screen of a tracking result by the overturn detection system according to an embodiment.

<Data Stored in Sensor>
  sensor ID
  pattern data (center pattern data)
  processing status (position)
  data indicating whether turnover occurred
  status No. of occurrence of turnover
  date and time of occurrence of turnover
  shipping goods (product) code
  shipping goods (product) data
  owner of goods (shipper) No.
  product received No.
  client usage No.
<Data Stored in Cellular Phones>
  GPS data of terminal device
  time data of terminal device
  temperature data of terminal device
  operator data of terminal device
<Data Stored as Server SV Storage Data>
  sensor ID
  pattern data (center pattern data)
  processing status (position)
  data indicating whether turnover occurred
  status No. of occurrence of turnover
  date and time of occurrence of turnover
  shipping goods (product) code
  shipping goods (product) data
  client usage No.
  GPS data of terminal device
  time data of terminal device
  temperature data of terminal device
  operator data of terminal device
  user ID of terminal device and password data FIG. 17 is an example screen of a tracking result by the overturn detection system according to this embodiment. Based on the data stored in the sensor, cellular phones Ta, Tb, and Tc, and server SV, the overturn detection system 2 may provide tracking data of each product.

To utilize the screen, the manager of the cellular phone clicks the icon for this system on the screen of the cellular phone. By doing this, an input screen to input user ID and password PW is displayed. The user ID and password PW are previously stored in the server SV. After the authentication is successfully performed, the manager is allowed to use the tracking screen of the overturn detection system 2 in this embodiment.

After the successful authentication, the terminal device such as the cellular phone may use the data displayed on the tracking screen and transmit route data of the product to the server SV. In this case, the receiving section 705 may receive the route data of the product from the terminal device, and the determination section 720 may determine the site where the overturn detection device 1 occurred based on the received route data.

Further, after the successful authentication, the terminal device may transmit the data indicating the state of the product to the server SV. In this case, the receiving section 705 may receive the data indicating the state of the product from the terminal device, and the determination section 720 may determine the state of the turnover of the overturn detection device 1 that occurred based on the data indicating the state of the product.

Figure 18:
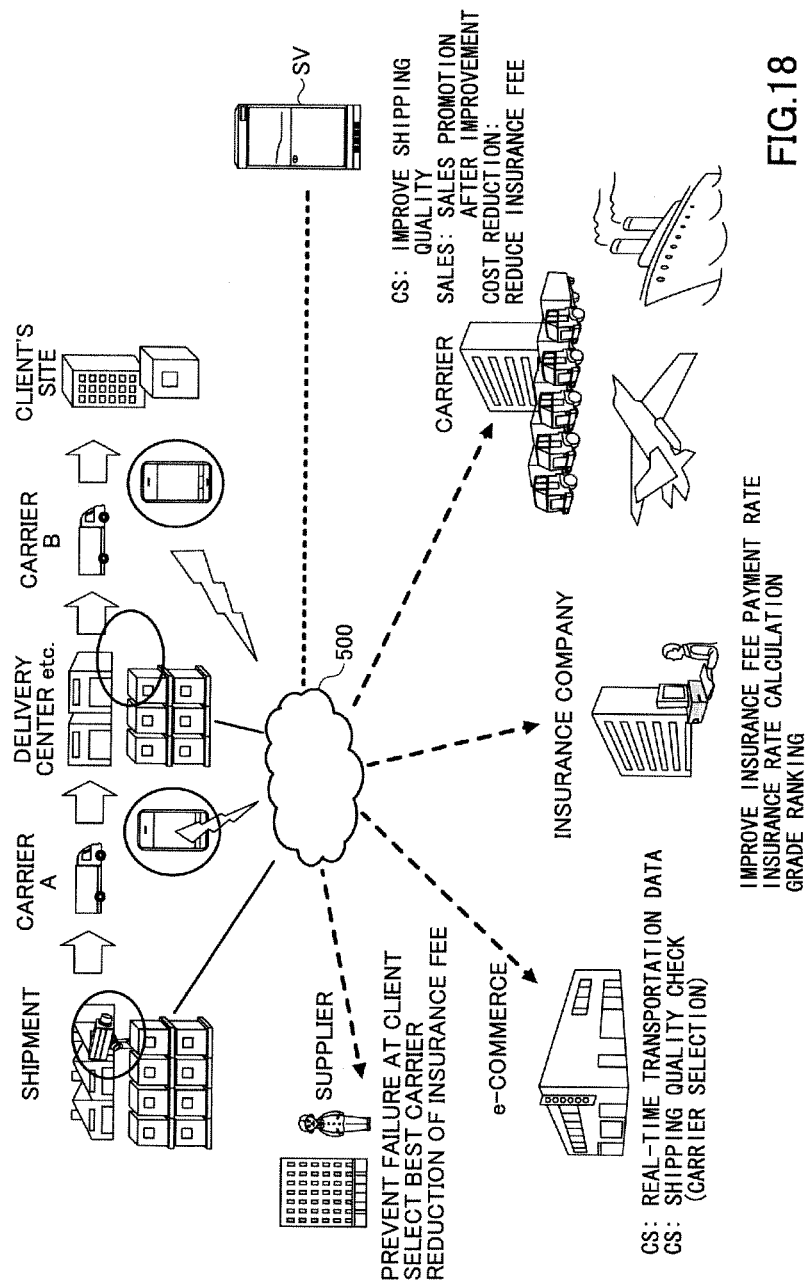
FIG. 18 illustrates an example application of the overturn detection system according to an embodiment.
Figure 19:
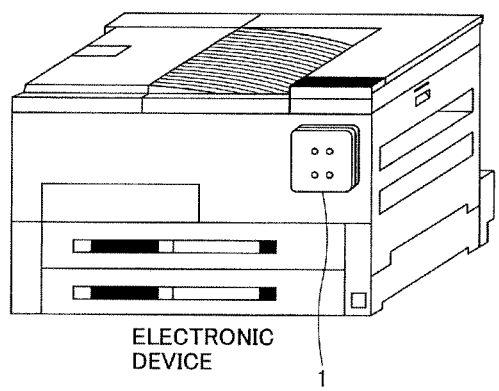
FIG. 19 illustrates an example electronic device including the overturn detection device according to an embodiment.

FIG. 18 illustrates an example application of the overturn detection system 2 according to an embodiment. In the overturn detection system 2, the server SV intensively manages the determination whether turnover occurred and the storage of data.

Therefore, for example, the determination results may be transmitted to a production and logistic system management company to be used for the logistic management of the production and logistic system management company. Further, the data may also be used for a billing system if the product is damaged or the like due to the turnover.

Further, in the above descriptions, cases are described where the overturn detection device is not directly included in an electronic device. However, the present invention is not limited to this configuration. Namely, for example, the overturn detection device may be included in (integrated into) an electronic device (electronic apparatus).

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth (i.e., the overturn detection device or the overturn detection system according to an embodiment of the present invention).

Further, each of the server and the terminal device according to an embodiment of the present invention includes a central processing unit (CPU) (not shown). The program that realizes the functions to be performed by the CPU may be previously stored in a storage (not shown) such as a ROM, or an HDD in a computer (not shown).

The program may be recorded in a recording medium such as a CD-ROM or a flexible disk or a non-volatile recording medium (memory) such as an SRAM, EEPROM or memory card. The functions of the server SV may be realized by causing the CPU to execute the program stored in such a memory. Further, the program may be downloaded via a network from an external device having a recording medium storing the program or a external device having a storage storing the program.

What is claimed is:

1. An overturn detection device comprising:
a housing including four or more display windows;
a back-forth direction detector installed on a first position of the housing and configured to display a position of a first detection member in a first display part, the first detection member being moved and held in response to turnover of the overturn detection device in the back and forth direction; and
a left-right direction detector installed on a second position of the housing and configured to display a position of a second detection member in a second display part, the second detection member being moved and held in response to turnover of the overturn detection device in the left and right direction,
wherein the installation positions of the back-forth direction detector and the left-right direction detector in the first and the second positions are not externally and visually recognizable, and
wherein at least a part of the first and the second display parts are displayed through the four or more display windows as pattern data.

2. The overturn detection device according to claim 1, further comprising
a storage unit configured to store identification data of the overturn detection device displaying the pattern data.

3. The overturn detection device according to claim 1, wherein the first and the second positions are changeable, and
wherein when at least one of the first and the second positions is changed, the pattern data displayed via the four or more display windows is changed.

4. The overturn detection device according to claim 1, wherein the four or more display windows are formed on the housing so that the distances between the display windows are determined in accordance with display positions of the first and the second display parts.

5. An overturn detection system for detecting turnover of a product, comprising:
a terminal device;
a server; and
the overturn detection device according to claim 1 attached to the product,
wherein the terminal device is configured to acquire an image including the four or more display windows of the overturn detection device and identification data of the overturn detection device, and transmit the image and the identification data to the server,
wherein the server includes
a receiving unit configured to receive the image and the identification data from the terminal device,
a registration unit configured to register the identification information of the overturn detection device in association with initial pattern data of the overturn detection device, and
a determination unit configured to determine whether the overturn detection device has been turned over based on a result of a comparison between the initial pattern data corresponding to the received identification data from among the identification data of the overturn detection devices stored in the registration unit and the pattern data that is identified based on the image.

6. The overturn detection system according to claim 5, wherein the determination unit is configured to determine in which direction the turnover has occurred based on the first and the second positions by identifying the first and the second positions based on the initial pattern data registered in the registration unit.

7. The overturn detection system according to claim 5, wherein the registration unit is configured to register the identification data of the product with the overturn detection device attached thereto in association with the identification data of the overturn detection device, and
wherein the determination unit is configured to determine the product with the attached overturn detection device that is determined to have been turned over before based on the identification data of the product registered in the registration unit.

8. The overturn detection system according to claim 5, wherein the terminal device is configured to transmit route data of the product,
wherein the receiving unit is configured to receive the route data of the product from the terminal device, and
wherein the determination unit is configured to determine a site where the overturn detection device has been turned over based on the route data.

9. The overturn detection system according to claim 5, wherein the terminal device is configured to transmit data indicating a state of the product,
wherein the receiving unit is configured to receive the data indicating the state of the product from the terminal device, and
wherein the determination unit is configured to determine a turnover state of the overturn detection device based on the data indicating the state of the product.

10. The overturn detection system according to claim 5, wherein the terminal device is configured to encrypt and transmit the image,
wherein the receiving unit is configured to receive the encrypted image from the terminal device, and
wherein the registration unit is configured to encrypt and store the received identification data of the overturn detection device.

11. An electronic device comprising:
the overturn detection device according to claim 1.

* * * * *